US00PP12868P2

(12) United States Plant Patent
Hanes

(10) Patent No.: US PP12,868 P2
(45) Date of Patent: Aug. 20, 2002

(54) GERANIUM PLANT NAMED 'AMRI PINK II'

(75) Inventor: Mitchell Eugene Hanes, Morgan Hill, CA (US)

(73) Assignee: Goldsmith Plants, Inc., Gilroy, CA (US)

( * ) Notice: Subject to any disclaimer, the term of this patent is extended or adjusted under 35 U.S.C. 154(b) by 0 days.

(21) Appl. No.: 09/802,867

(22) Filed: Mar. 12, 2001

(51) Int. Cl.[7] ..... A01H 5/00

(52) U.S. Cl. ..... Plt./325

(58) Field of Search ..... Plt./324, 325, 328, Plt./329

*Primary Examiner*—Bruce R. Campell
*Assistant Examiner*—Kent L. Bell
(74) *Attorney, Agent, or Firm*—Rothwell, Figg, Ernst & Manbeck

(57) ABSTRACT

A geranium cultivar paricularly distinguished by dark green foliage, pink flower color, and semi-double flowers on large umbels, fast rooting and exhibits vigorous growth.

1 Drawing Sheet

GENUS AND SPECIES

*Pelargonium hortorum.*

VARIETY DENOMINATION

Figure 1:
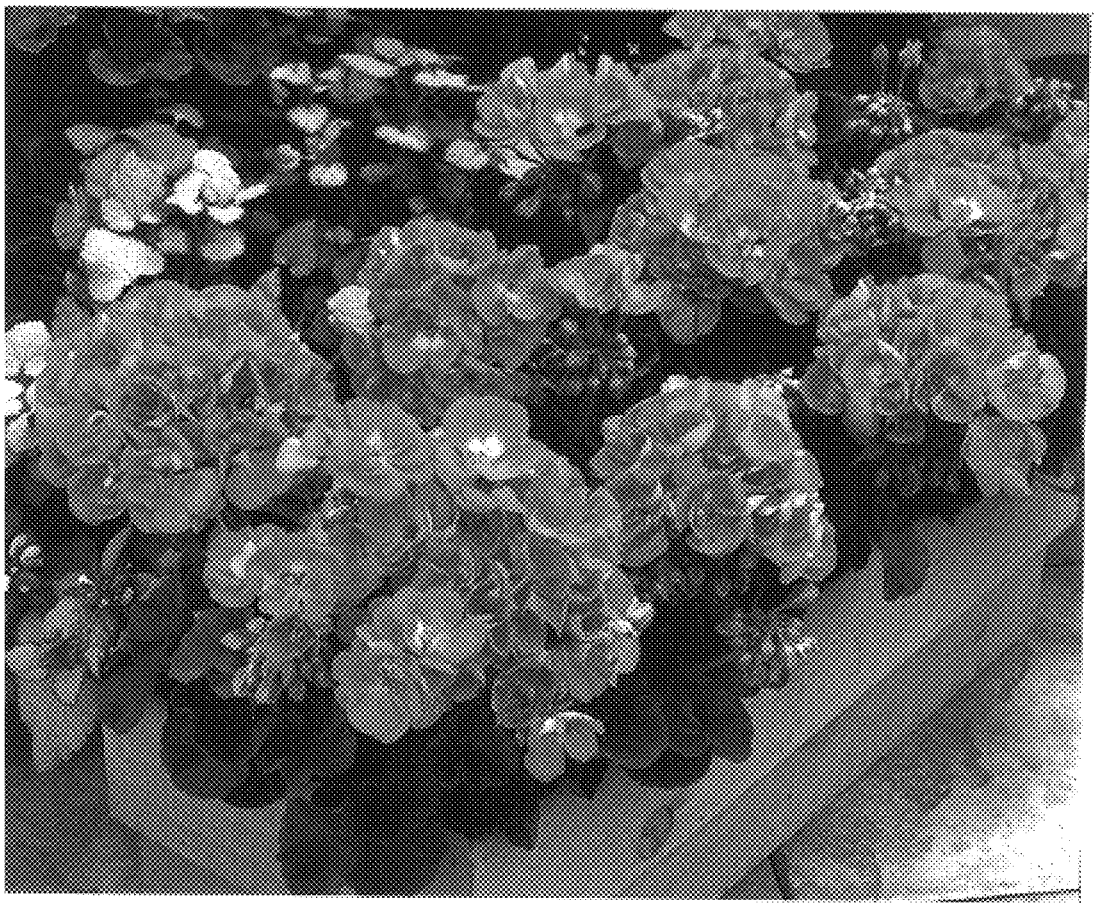

'Amri Pink II'.

BACKGROUND OF THE NEW PLANT

The present invention comprises a new and distinct cultivar of geranium, botanically known as *Pelargonium hortorum* Bailey, and hereinafter referred to by the cultivar name 'Amri Pink II'. The new cultivar is propagated from a seedling resulting from the cross of an unnamed and unpatented proprietary line known as 7059-2, seed parent, which is a pink single flowered dark leafed geranium and 'Designer Hot Pink' (U.S. Plant Pat. No. 8,525), pollen parent, which is a pink geranium.

'Amri Pink II' is a product of a planned breeding program intended to create new geranium cultivars with pink colored flowers, semi-double flower form, green foliage, vigorous growth and superior cutting productivity.

The new cultivar was created in 1997 in Gilroy, Calif. and has been repeatedly asexually reproduced by cuttings in Gilroy, Calif. and Guatemala over a three and a half year period. It has also been trialed at Gilroy, Calif., Okemos, Mich. and Andijk, The Netherlands. It has been found to retain its distinctive characteristics through successive propagations; and this novelty is firmly fixed.

DESCRIPTION OF PHOTOGRAPH

This new geranium plant is illustrated by the accompanying photograph which shows blooms, buds, and foliage of the plant in full color, the colors shown being as true as can be reasonably obtained by conventional photographic procedures.

FIG. 1 shows overall plant habit.

DESCRIPTION OF THE NEW CULTIVAR

The following detailed descriptions set forth the distinctive characteristics of 'Amri Pink II'. The data which defines these characteristics were collected from asexual reproductions carried out in Gilroy, Calif. The plant history was taken on five month old plants grown in 8 inch pots, blossomed under natural light in a greenhouse and color readings were taken in the greenhouse in Gilroy, Calif. Color references are primarily to The R.H.S. Colour Chart of The Royal Horticultural Society of London (R.H.S.).

DETAILED BOTANICAL DESCRIPTION

Classification:
*Botanical.*—*Pelargonium hortorum* Bailey.
*Commercial.*—Geranium.
Form: Upright, rounded, basal branched.
Height: From soil level to top of plant (excluding blooms) — 16 cm; from soil level to top of umbels — 20.5 cm.
Width: 30–35 cm.
Time to produce a finished flowering plant: 12 weeks.
Outdoor plant performance: Good heat tolerance, strong growth, maintains rounded habit.
Time to initiate roots: 7–8 days.
Time to develop roots: 25 days.
Root description: White, slightly pubescent, fibrous yet coarse.

The Leaves

Length: 8.5–9.5 cm.
Width: 5.0–6.0 cm depending on age.
Apex description: Rounded.
Base description: Cordate.
Shape: Reniform.
Margin: Crenate.
Texture: Leathery and pubescent on both surfaces.
Ribs and veins: Palmate (digitate), 2.5–5.0 cm long
Color: Upper side — Yellow-green RHS 146A; Under side — Yellow-green RHS 146B; Ribs and veins — Yellow-green RHS 146D.
Petiole length: 6.5–9.0 cm depending on age of the leaf.
Petiole diameter: 2–3 mm.
Petiole color: Yellow-green RHS 146C.
Lateral branch length: 6.5–7.0 cm.
Internode length: 5 mm–1 cm.
Lateral branch color: Yellow-green RHS 146D.

The Bud

Diameter: 7–8 mm.
Length: 1 cm.
Shape: Narrow elliptic.
Color when sepals first divide: Bright pink between RHS 58C and RHS 58D.
Number of sepals: 5.
Length of sepals: 11–12 mm.
Width of sepals: 3–4 mm.
Shape: Subulate as it tapers from base to apex.
Sepal color in an open flower: Upper and lower surfaces are green RHS 146D.

The Flower

Size: Approximately 5 cm in diameter.
Form: Polypetalous, cup shaped, later flattening to shallow cup shape.
Petals/petaloids: 5 petals, 3 petaloids; Shape: spatulate/oblanceolate.
Apex shape: Obtuse.
Base shape: Cuneate.
Margin: Entire.
Petal color:
*Upper surface.*—Pink RHS 57D with a white eye of RHS 155D and faint stripes of pink RHS 57D through the white eye.
*Lower surface.*—Pink RHS 62A.
Petaloid color:
*Upper.*—Pink RHS 57D.
*Lower.*—Pink RHS 57D.
Color change with age: Minimal.
Pedicel length: Approximately 2.5–3.0 cm.
Pedicel color: Yellow-green RHS 152D with a dark red RHS 59B overcast on the upper side.
Flower persistence: An open flower will hold its petals until the flower begins to dehisce, or approximately 7–10 days.

The Inflorescence

Type: An umbel composed of approximately 25 flowers.
Diameter: 9–10 cm.
Depth: 6.5 cm.
Peduncle length: 11–12 cm.
Peduncle color: Yellow-green RHS 144A.

The Reproductive Organs

Anthers: 5–6.
Anther color: Salmon RHS 37B prior to anthesis.
Filament color: Base is White RHS 155D with pink RHS 57C at apex.
Pollen amount and color: Moderate, orange RHS 25A.
Pistil: 1 with a length of 8 mm.
Stigma: 5 linear lobes with a color of pink RHS 52B.
Style: 3 mm in length with a color of pink RHS 52B.
Ovary: At anthesis, densely pubescent with white hairs, oblong, green drying to a light brown at maturity.
Seed number: Maximum of 5 per spike.
Seed length: 4–5 mm.
Seed width: 1.5–2.0 mm.
Seed color: Brown RHS 165A, may darken with age.

Disease and Insect Resistance

No susceptibility to diseases or insects noted to date.

Comparison with Known Cultivars

'Amri Pink II' has semi-double flowers versus a single flower for 7059-2. 7059-2 also has darker foliage than 'Amri Pink II'. 'Designer Hot Pink' produces a larger plant and is a darker shade of pink than 'Amri Pink II'.

I claim:

1. A new and distinct cultivar of geranium plant as shown and described herein.

* * * * *